United States Patent [19]

Fujise et al.

[11] Patent Number: 5,588,036

[45] Date of Patent: Dec. 24, 1996

[54] X-RAY CT APPARATUS AND RADIOGRAPHING METHOD USING SAME

[75] Inventors: Masakuni Fujise, Otawara; Hiroshi Ishikawa, Mitaka, both of Japan

[73] Assignee: Kabushiki Kaisha Toshiba, Kawasaki, Japan

[21] Appl. No.: 601,967

[22] Filed: Feb. 15, 1996

Related U.S. Application Data

[63] Continuation of Ser. No. 266,631, Jun. 28, 1994, abandoned.

[30] Foreign Application Priority Data

Jun. 28, 1993 [JP] Japan ...................................... 5-157470

[51] Int. Cl.⁶ ............................................................ G21K 5/10
[52] U.S. Cl. .................................................. 378/146; 378/4
[58] Field of Search ......................................... 378/4, 8, 98.5, 378/98, 146, 901

[56] References Cited

U.S. PATENT DOCUMENTS

| | | | |
|---|---|---|---|
| 5,018,178 | 5/1991 | Katsumata | 378/8 |
| 5,349,625 | 9/1994 | Born et al. | 378/146 |

*Primary Examiner*—Don Wong
*Attorney, Agent, or Firm*—Oblon, Spivak, McClelland, Maier & Neustadt, P.C.

[57] ABSTRACT

A radiographing operation is performed by using an X-ray CT apparatus for performing a radiographing operation to a subject lying on a bed, which comprises a bed drive means, an X-ray tube irradiating an X-ray to the subject, a detecting means for detecting an irradiated X-ray, a gantry on which said X-ray tube and said X-ray detecting means are mounted, a gantry drive means for rotationally driving the gantry, an exposure information file means into which past exposure information for the subject is stored, and a main controller for controlling the X-ray tube, the bed drive means and the gantry drive means. The radiographing condition according to which the radiographing operation is performed is set in accordance with a past exposure information stored in the exposure information file and at least one of the bed, the X-ray tube and the gantry.

18 Claims, 5 Drawing Sheets

5,588,036

X-RAY CT APPARATUS AND RADIOGRAPHING METHOD USING SAME

This application is a continuation of application Ser. No. 08/266,631, filed on Jun. 28, 1994, now abandoned.

BACKGROUND OF THE INVENTION

1. Field of the Invention

The present invention relates to an X-ray CT apparatus and a radiographing method for setting radiographing conditions at a time of radiographing by using the X-ray CT apparatus.

2. Related Prior Art

An X-ray CT (computerized tomography) apparatus has been widely used as a medical diagnosis apparatus for providing a tomographic image of a body of a subject such as a patient.

When radiographing operation is performed by using an X-ray CT apparatus, various radiographing conditions such as a scan speed, tube voltage, tube current, slicing width, scan pitch, and tilt angle are entered in advance as previous informations, and a scanning operation is then carried out in accordance with the entered radiographing conditions to obtain a desired tomographic image.

In such medical use, there is a case where a particular region of a patient is repeatedly radiographed at regular intervals in order to determine time-dependent changes such as progress or healing of a disease of a patient. In such a case, the radiographing has been often carried out under nearly the same radiographing conditions as those by which the previous radiographing was carried out for the reason that the subject, the region to be diagnosed, the type of disease, etc. are the same.

In a conventional X-ray CT apparatus, however, the radiographing conditions must be reset each time the radiographing is performed. This is extremely troublesome to an operator and causes the examination efficiency to be lowered.

SUMMARY OF THE INVENTION

An object of the present invention is to substantially eliminate defects or drawbacks encountered in the prior art and to provide an X-ray CT apparatus and a radiographing method using the X-ray CT apparatus capable of automatically setting radiographing conditions in accordance with past exposure information of a subject.

This and other objects can be achieved according to the present invention by providing, in one aspect, an X-ray CT apparatus for performing a radiographing operation to a subject lying on a bed, comprising:

a bed drive means for moving a bed to a predetermined position;

an X-ray tube irradiating an X-ray to the subject;

a detecting means for detecting an irradiated X-ray;

a gantry means on which the X-ray tube and the X-ray detecting means are mounted;

a gantry drive means for rotationally driving the gantry means;

an exposure information file means into which past exposure information for the subject is stored; and a main controller for setting a radiographing condition in accordance with the past exposure information stored in the exposure information file and for controlling at least one of the X-ray tube, the bed drive means and the gantry drive means in accordance with the set radiographing condition.

In a preferred embodiment in this aspect, the apparatus further comprises a bed drive means controller, a gantry drive means controller and a high-voltage controller, through which the bed drive means, the gantry drive means and the X-ray tube are controlled, respectively, by the main controller. The main controller comprises a central processing unit, a scan control means for controlling the high-voltage controller, the bed drive means controller and the gantry drive means controller, an input/output control means for the exposure information file means and means for converting a slice information data within the exposure information into a slice information image data and controlling the data for display, the scan control means, the input/output control means and the converting means are operatively connected to the central processing unit. A monitor is operatively connected to the data converting and controlling means of the main controller, the monitor means including a main monitor for displaying a scanographic image and a sub-monitor for displaying the exposure information as numerical data.

In another aspect of the present invention, there is provided a method for performing a radiographing operation by using an X-ray CT apparatus of the characters described above, wherein a radiographing condition according to which the radiographing operation is performed is set in accordance with a past exposure information stored in the exposure information file and at least one of the bed, the X-ray tube, and the gantry in accordance with the set radiographing conditions.

In one preferred embodiment, the radiographing operation is performed by the steps of:

preparing an information of the subject;

entering the information into the main controller;

indexing the past exposure information of the subject from the exposure information file;

confirming whether the past exposure information is indexed;

displaying the indexed past exposure information as numerical data in a case where the past exposure information is indexed;

confirming whether a radiographing condition is set in accordance with the displayed exposure information;

setting and storing the radiographing condition in a case where the radiographing condition is set in accordance with the displayed exposure information; and performing a scan operation with the set radiographing condition.

In this embodiment, the radiographing operation further comprises the steps of modifying a numerical data of the radiographing condition in the displayed exposure information. In a case where the past exposure information is not indexed, the radiographing condition is set manually and stored and the scan is then performed with the set radiographing condition. In a case where the radiographing condition is not set, it is confirmed whether further index is to be continued and in a case where the index is continued, another past exposure information for the subject is further indexed, and in a case where the index is not continued, the radiographing condition is set manually and stored.

In another preferred embodiment, the radiographing operation is performed through a previous setting of a radiographing position and region of the subject by the steps of:

preparing an information of the subject;

entering the information into the main controller;

carrying out a scanographing operation and displaying the scanographic image on the monitor;

indexing the past exposure information of the subject from the exposure information file;

confirming whether the past exposure information is indexed;

converting a slice information in the indexed past exposure information into a slice information image data in a case where the past exposure information is indexed;

displaying the indexed past exposure information as numerical data and displaying the slice information as slice information image data;

confirming whether a radiographing condition is set in accordance with the displayed exposure information;

inversely converting the slice information image data into the slice information;

setting and storing the radiographing condition in a case where the radiographing condition is set in accordance with the displayed exposure information; and performing a scan operation with the set radiographing condition.

In this embodiment, the radiographing operation further comprises the step of modifying a numerical data of the radiographing condition and the slice information image data in the displayed exposure information.

In a case where the past exposure information is not indexed, the radiographing condition is set manually and stored and the scan is then performed with the set radiographing condition. In a case where the radiographing condition is not set, it is confirmed whether further index is to be continued and in a case where the index is continued, another past exposure information for the subject is further indexed, and in a case where the index is not continued, the radiographing condition is set manually and stored.

In the above embodiments, a predetermined number of a plurality of past exposure informations for the subject are stored in accordance with the time order and when a new radiographing condition is stored as exposure information, an oldest past exposure information automatically vanishes.

According to the embodiments of the present invention, the past exposure information on a particular subject such as a patient is indexed from the exposure information file, which stores exposure information.

Then, the radiographing conditions are set based on the indexed past exposure information. Scan is then carried out while controlling at least one of the bed, the X-ray tube, and the gantry in accordance with the set radiographing conditions.

According to the preferred embodiment of the present invention, scanography is performed to produce a scanographic image before implementing the scan. The slice information such as the slicing pitch in the slicing operation and the tilt angle of the gantry is converted to slice information image data, and the converted slice information image data are displayed on a monitor as an image which is superimposed on the scanographic image.

At this point, no relationship of relative position has been established between the slice information image and the scanographic image on the monitor.

Next, the slice information image is modified so that the radiographing will be carried out at a desired point on the scanographic image and at a desired tilt angle.

As a mode of modifying the slice information image, the whole slice information image is moved on the monitor with respect to the scanographic image. Such a modifying operation on the monitor establishes the relationship of relative position between the slice information image and the scanographic image.

Then, the modified slice information image data are inversely converted to the slice information data, and the inversely converted slice information data and numerical data, which have been modified separately, are used as the radiographing conditions for carrying out the scan. During the scan, the gantry, the bed, and the X-ray tube are controlled in accordance with the radiographing conditions.

The nature and further features of the present invention will be made more clear from the following descriptions made with reference to the accompanying drawings.

DESCRIPTION OF THE PREFERRED EMBODIMENT

Figure 1:
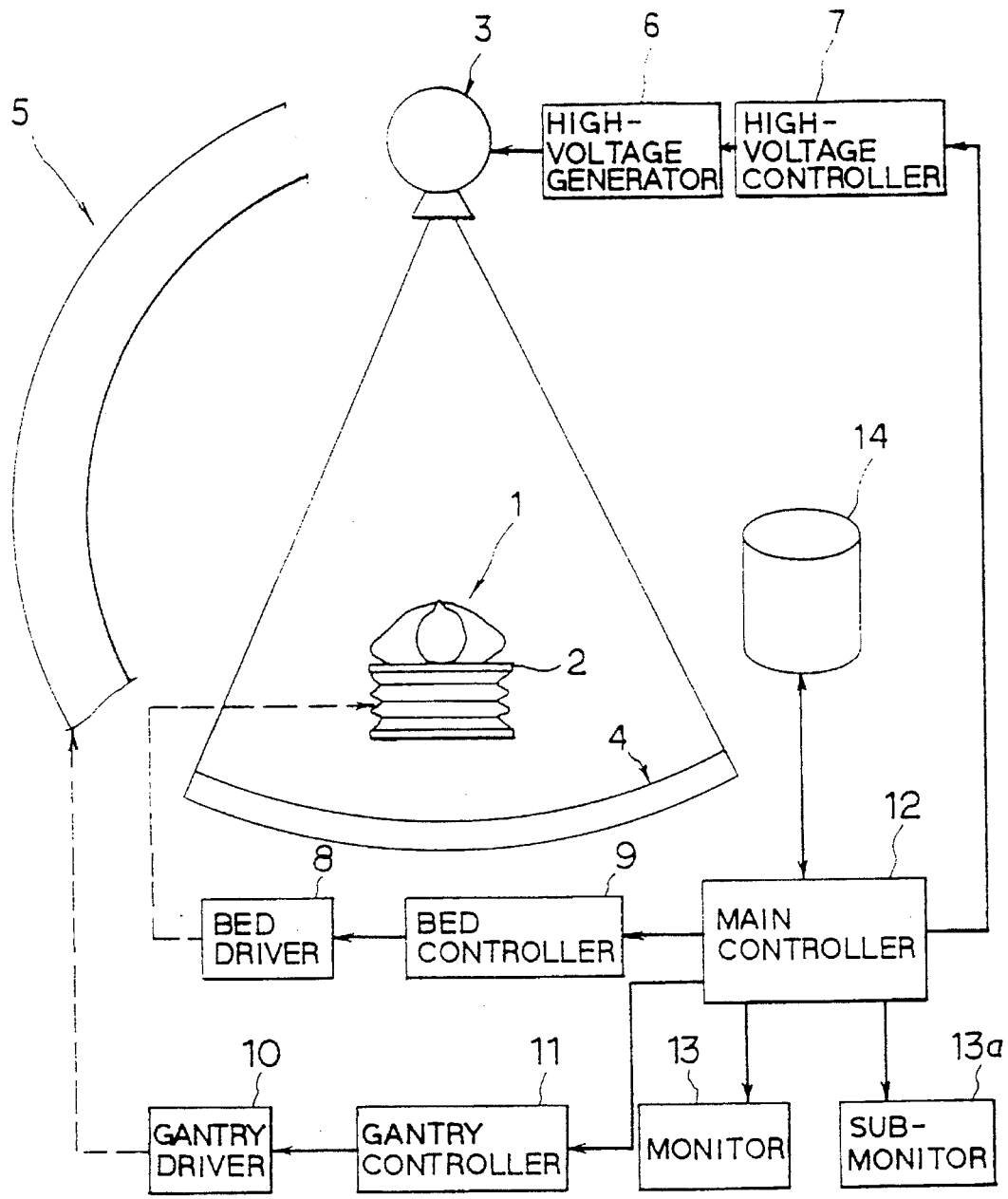
FIG. 1 is a block diagram of the X-ray CT apparatus of the present invention.

FIG. 1 is a block diagram showing an X-ray CT apparatus according to the embodiment of the present invention. Referring to FIG. 1, a subject, i.e. a patient, 1 lies on a bed 2 which is movable horizontally and vertically by a known drive means. The X-ray CT apparatus comprises an X-ray tube 3, which irradiates an X-ray to the patient 1 and an X-ray detector 4, which detects the irradiated X-ray. The X-ray tube 3 and the X-ray detector 4 are mounted on a gantry or frame 5 which can be turned around a predetermined axis of rotation.

The X-ray CT apparatus of the embodiment is also equipped with a high-voltage generator 6 for generating high voltage to be applied to the X-ray tube 3, a high-voltage controller 7 for controlling the high-voltage generator 6, a bed drive unit 8 for driving the bed 2 and a bed controller 9 for controlling the bed drive unit 8.

The X-ray CT apparatus of this embodiment is further equipped with a gantry drive unit 10 for rotating the gantry 5 around a predetermined axis of rotation and a gantry controller 11 for controlling the gantry drive unit 10. The X-ray CT apparatus of the embodiment still further comprises a main controller 12, which controls the high-voltage controller 7, the bed controller 9, and the gantry controller 11. A monitor 13 for displaying a desired image and a sub-monitor 13a for displaying the radiographing conditions are also equipped, and these monitors 13 and 13a are also operatively connected to the main controller 12.

The main controller 12 indirectly controls the X-ray tube 3, the bed 2, and the gantry 5 so that the X-ray tube 3 irradiates a predetermined X-ray. The bed 2 moves to a predetermined position or at a predetermined speed, and the gantry 5 rotates at a predetermined rotational speed or at a predetermined tilt angle.

The X-ray CT apparatus of this embodiment further comprises an exposure information file 14, in which exposure information data is stored as a disk or the like, and the main controller 12 is designed to set radiographing conditions according to past exposure information data stored in the exposure information file 14 and controls the bed 2, the X-ray tube 3, and the gantry 5 in accordance with the set radiographing conditions. The exposure information data may be directly inputted into the controller 12 through an on-line system.

Figure 2:
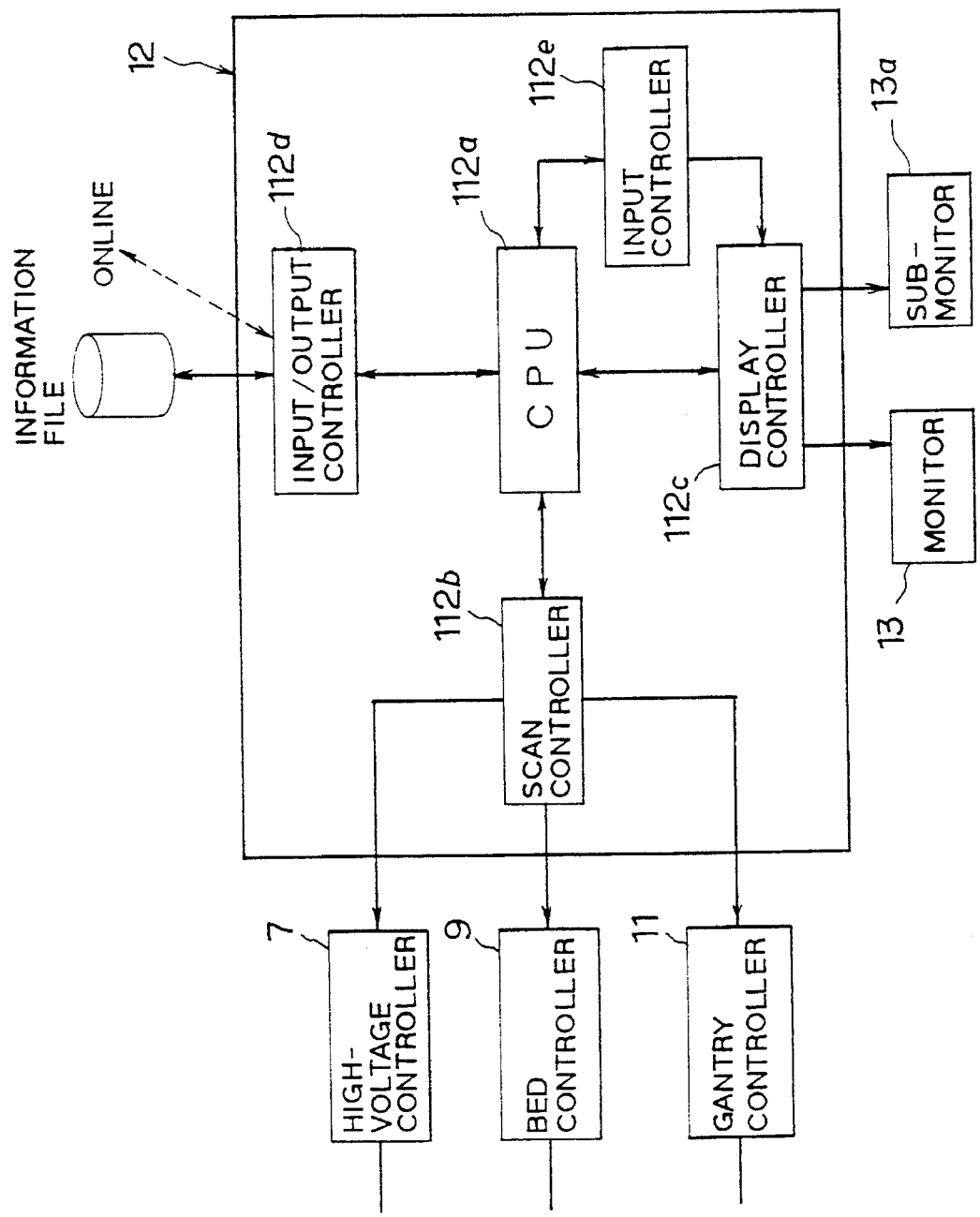
FIG. 2 is a brief block of a main controller of the apparatus of FIG. 1.

In the above meanings, the main controller 12 comprises the following elements as shown in FIG. 2. The main controller 12 comprises a central processing unit (CPU) 112a, a scan control element 112b giving instructions to the high voltage control 7, the bed drive controller 9 and the gantry controller 11, a display control element 112c giving instructions to the monitor 13 and the sub-monitor 13a, and an input/output control element 112d for the exposure information file 14. These elements 112b, 112c and 112d are operatively connected to the CPU 112a. An input control element 112e may be disposed between the CPU 112a and the display control element 112c. The functions of the controller 12 including these elements will be made more clear hereinafter with reference to the flowchart of FIG. 3.

The exposure information file 14 stores exposure information, including the ID of a patient, the name of the patient, the date of exposure, scan mode, the number of the scans, a radiographed area, a scan speed, a tube voltage, a tube current, a slicing width, a reconstruction function, a posture of the patient, a direction of inserting the patient, a direction of observation, a use of a contrast medium, a type of voice, a relative table position, a tilt angle, a pause time between scans, and a scan pitch.

The tilt angle refers herein to the angle of the tilt of the gantry 5 from a predetermined reference axis (the vertical direction when the X-ray CT apparatus is normally disposed). A zero tilt angle, for example, indicates that the slice plane is set in a direction perpendicular to the body axis of a patient. The scan pitch refers to the distance between adjoining slices.

The main controller 12 is capable of converting, out of the exposure information, the data showing the slice-related information, that is, the number of slices, the tilt angle and the scan pitch (hereinafter referred to totally as "slice information data"), into graphic data (hereinafter referred to as "slice information image data"), which can be displayed on a scanographic image in a superimposed manner, and the desired slice information image data is inversely converted to the slice information data.

The operation of the X-ray CT apparatus of the present invention will be described hereunder.

Figure 3A:
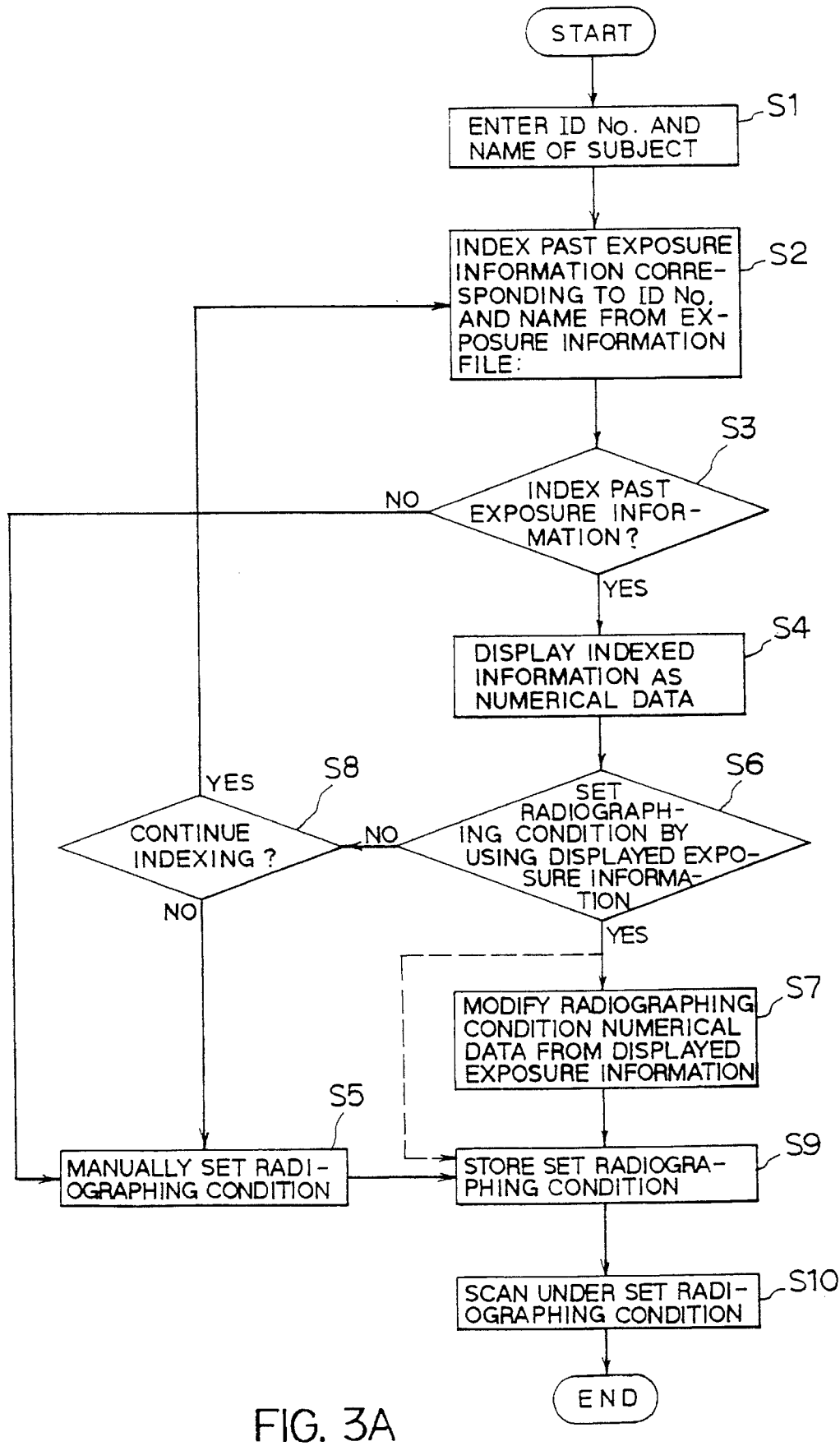
FIG. 3 (3A and 3B) is a flowchart, which shows a procedure for setting the radiographing conditions by using the X-ray CT apparatus of the present invention.
Figure 3B:
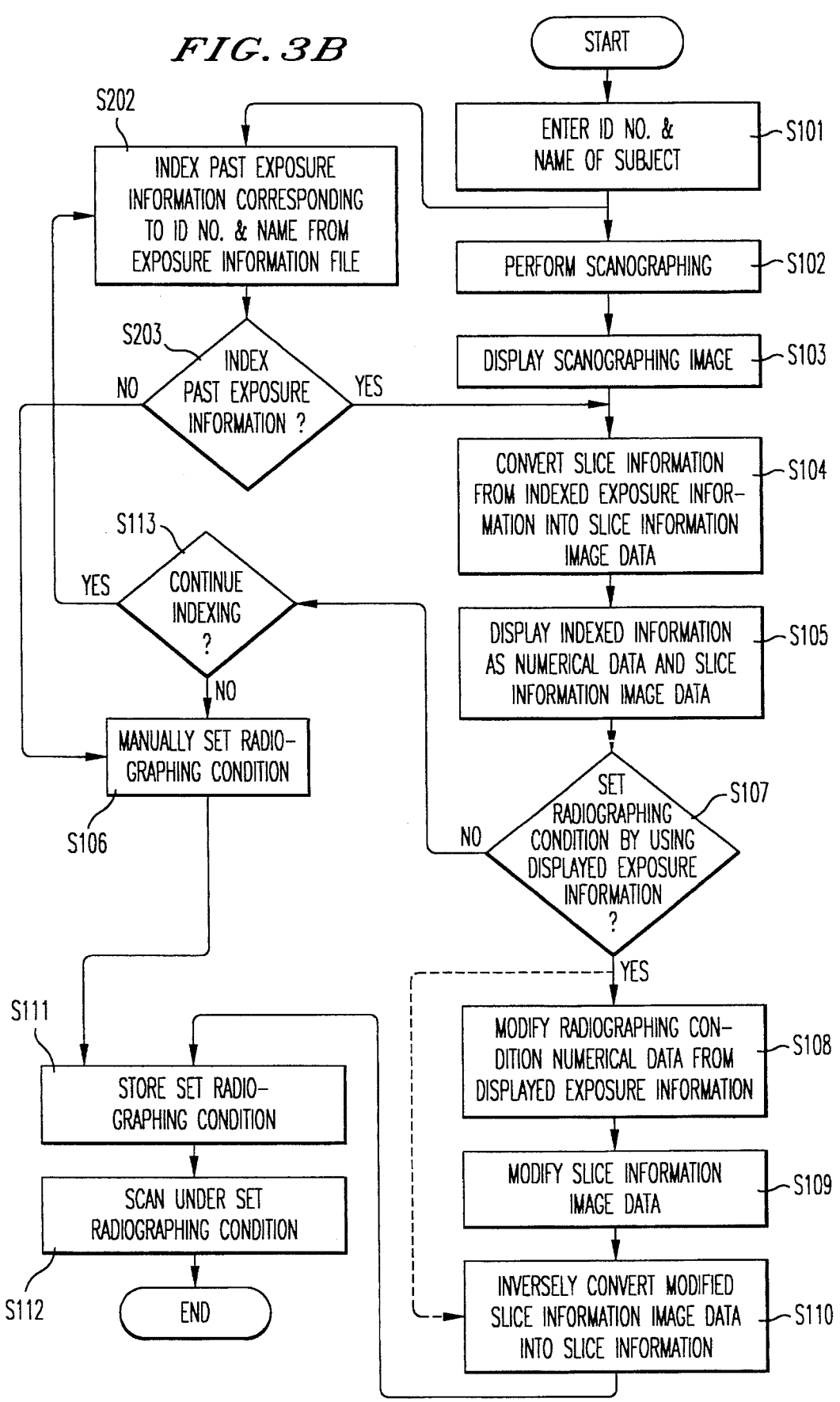

FIGS. 3A and 3B are flowcharts showing the procedure for setting radiographing conditions by using the X-ray CT apparatus, in which the flowchart of FIG. 3A represents the case requiring no scanographing operation and FIG. 3B represents the case requiring the scanographing operation.

First, with reference to FIG. 3A, identification (ID) number and name of a subject such as patient are entered at a step S1, and past exposure information data corresponding to the ID No. and the name of the patient is indexed by the main controller 12 from an exposure information file stored in the information exposure file 14 at step S2. In the next step S3, it is confirmed whether the past exposure information is indexed or not. In the case of "YES", the indexed information is displayed on the display sub-monitor 13a (step S4) as numerical data, and in the case of "NO", the radiographing conditions are manually set (step S5).

In a step S6, it is confirmed whether the radiographing conditions are set by utilizing the displayed exposure information or not. In the case of "YES", the set radiographing conditions are set and stored in the file 14 in a step S9, and in this operation, when it is required to modify the numerical data of the radiographing conditions, such modification or correction will be done in a step S7 before the step S9.

In the step S6, in the case of "NO", it is confirmed whether the indexing is to be carried out continuously or not (step S8), and in the case of "NO", the radiographing conditions are manually set as referred to in the step S5. In the case of "YES", the step returns to the step S2 to again carry out the indexing of the another past exposure information of the same patient from the stored exposure information file and continue the same operations as those described above.

In the final step S10, the scanning operation is carried out under the set and stored radiographing conditions under the controlling of the main controller 12 through the high voltage controller 7, the bed controller 9 and the gantry controller 11 for controlling the setting conditions of the high voltage generator 6 for the X-ray tube 3, the patient bed 2 and the gantry 4.

On the other hand, in the case where a previous scanographing is required for setting radiographing position and range of the patient, the operation will be performed in accordance with the flowchart of FIG. 3B.

With reference to FIG. 3B, identification (ID) number and name of a subject such as patient are entered at a step S101 and a scanographing is preliminarily performed for setting the position and the region of the patient to be radiographed in the next step S102. The thus obtained scanographic image is displayed on the monitor 13 at a step S103. In parallel to these steps S102 and S103, other steps S202 and S203, which corresponding to the step S2 and S3 are performed, that is, the past exposure information data corresponding to the ID No. and the name of the patient are indexed by the main controller 12 from an exposure information file stored in the information exposure file 14 at the step S202. In the next step S203, it is confirmed whether the past exposure information is indexed or not. In the case of "YES", the information from the Step S103 is combined, and a slice information from the indexed exposure data is converted to a slice information image data in a step S104 by the main controller 12 and the indexed information is displayed (step S105) as numerical data on the sub-monitor 13a and slice information image data on the monitor 13 by superimposing it on the scanographic image.

Figure 4A:
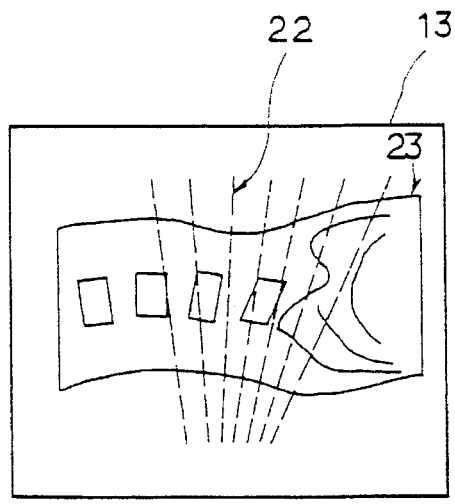
FIG. 4A shows the slice information image data displayed on the scanographic image in a superimposed manner.
Figure 4B:
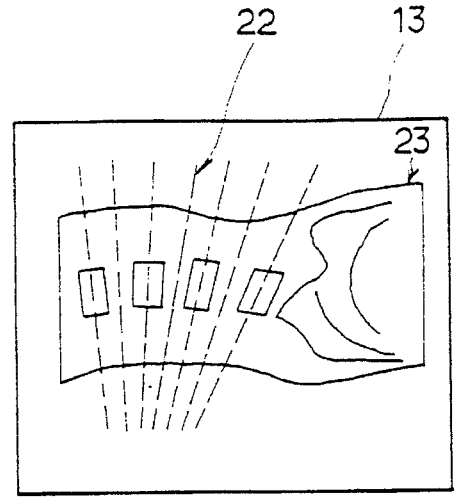
FIG. 4B shows a mode of modifying the slice information image data.
Figure 4C:
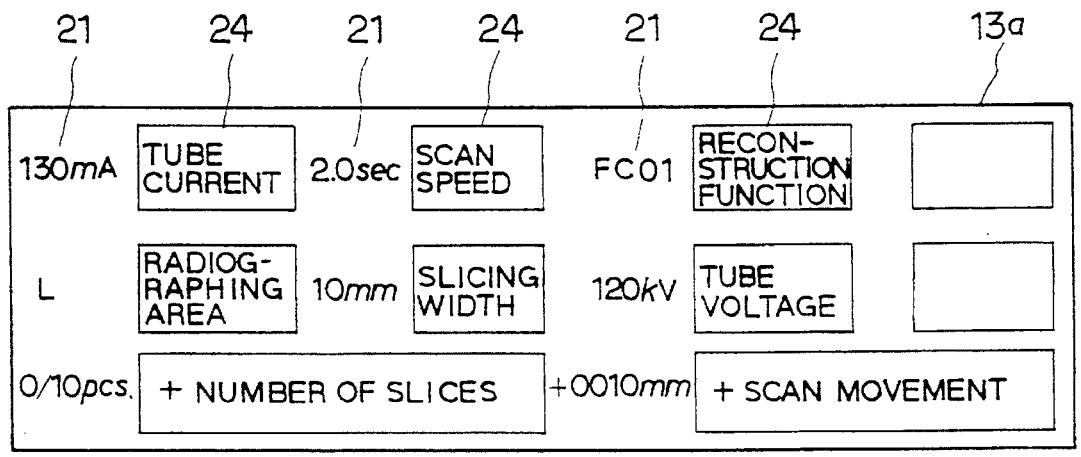
FIG. 4C shows the numerical data displayed on a sub-monitor.

In connection with this step, FIG. 4A shows the slice information image data 22, which is displayed in a superimposed manner on the scanographic image 23 on the monitor 13. At this point, no relationship of relative position has been established between the slice information image and the scanographic image on the monitor. FIG. 4C shows the numerical data 21 displayed on the sub-monitor 13a.

In the step S203, in the case of "NO", the radiographing conditions are manually set (step S106).

In a step S107, it is confirmed whether the radiographing conditions are set by utilizing the displayed exposure information on the sub-monitor 13a or not. In the case of "YES", the radiographing conditions are set and stored in a step S111. However, this step S111 will be done through the following steps S108 to S110 in a case where it is required to modify or correct the numerical data of the radiographing conditions of the displayed exposure information regarding such as the tube current, tube voltage, scanning speed, etc., the modification is performed in a step S108. In this modification, if, for example, a touch-panel type EL display is used as the sub-monitor 13a, a switch 24 may be installed beside the section where the numerical data 21 to be modified is displayed, and the new numerical data can be set by pressing the switch 24. Furthermore, in a case of requiring the modification or correction of the slice information image data, the radiographing operation is performed with a desired tilt angle. This is performed in a step S109, and the modified or corrected slice information image data is inversely converted into the slice information (step S110). This step S110 will be performed in the case of no modification for inversely converting the data to the slice information. In the step S109, reference is to be made to FIG. 4B showing one mode of modifying the slice information image data. As is apparent from the comparison with FIG. 4A, the whole slice information image has been moved on the monitor with respect to the scanographic image, and next, the modified data is inversely converted as mentioned above.

In the step S107, in the case of "NO", it is confirmed whether the indexing is to be carried out continuously or not (step S113), and in the case of "NO", the radiographing conditions are manually set as referred to in the step S106. In the case of "YES", the step returns to the step S202 to again carry out the indexing of the past exposure information of the same patient from the stored exposure information file and continue the same operations as those described above.

In the final step S112, the scanning operation is carried out under the set and stored radiographing conditions under the controlling of the main controller 12 through the high voltage controller 7, the bed drive controller 9 and the gantry controller 11 for controlling the setting conditions of the high voltage of the X-ray tube 3, the patient bed 2 and the gantry 4.

In the above operation steps, in a preferred embodiment of the present invention, a plurality of past exposure information data of one patient are stored in the file with respect to the respective portions to be exposed in a predetermined file position in a manner such that when a new information is stored, the oldest information is automatically vanished, and accordingly, the same numbers of the past exposure information data are stored in accordance with the passing of time.

As described above, the X-ray CT apparatus of the present invention is designed to automatically set the radiographing conditions in accordance with the past exposure information. This achieves higher examination efficiency and reduced burden on the operator.

Further, in the above embodiment, the whole slice information image data are moved as one mode of modifying the slice information image data, but it is needless to say that there is no need to move the slice information image data if the slice happens to be set at the desired radiographing point.

Furthermore, only the tilt angle of a particular slice may be modified or the scan pitch of a particular section may be modified.

In the embodiment described above, the exposure information file is provided separately from the main controller, but it may alternatively be provided in a disk inside the main controller.

Moreover, a single exposure information file may be configured so that it may be shared by a plurality of X-ray CT apparatuses through, for example, a network.

What is claimed is:

1. An X-ray CT apparatus for performing a scanning operation on an examined region of a patient lying on a bed, in which an X-ray from an X-ray tube irradiating the patient passes through the patient and is detected by a detecting means, the X-ray CT apparatus comprising:

a scan condition file means into which past scan condition including a predetermined scan pitch and a predetermined slicing width for patients to be scanned are stored, the past scan condition being acquired by means of previously performing at least one scanning operation on the examined region of the patient;

means for individually designating a specific one of the patients;

means for reading out the past scan condition of the designated specific one of the patient from the scan condition file means; and a main controller for setting a scan condition in accordance with the past scan condition of the examined region of the designated patient and for performing the scanning operation on the examined region of the designated patient in accordance with the set scan condition.

2. An X-ray CT apparatus according to claim 1, further comprising a bed drive means controller, a gantry drive means controller and a high-voltage controller, through which said bed drive means, said gantry drive means and said X-ray tube are controlled, respectively, by the main controller.

3. An X-ray CT apparatus according to claim 2, wherein said main controller comprises a central processing unit, a scan control means for controlling said high-voltage controller, said bed drive means controller and said gantry drive means controller, an input/output control means for said scan condition file means and means for converting a slice information data within the exposure information into a slice information image data and controlling the data for display, said scan control means, said input/output control means and said converting means are operatively connected to said central processing unit.

4. An X-ray CT apparatus according to claim 3, further comprising a monitor means operatively connected to the means for converting data and controlling data for display of the main controller, said monitor means including a main monitor for displaying an image information and a sub-monitor for displaying the exposure information as numerical data.

5. An X-ray CT apparatus according to claim 1, wherein each of said past scan condition includes a number of scans, scanned area, a tube voltage of the X-ray tube, and a tube current of the X-ray tube.

6. A method of performing a scanning operation on an examined region of a patient lying on a bed using an X-ray CT apparatus, wherein said method comprises the steps of:

preliminary storing past scan condition including a predetermined scan pitch and a predetermined slicing width for patients to be scanned into a scan condition file, the past scan condition being acquired by means of previously performing at least one scanning operation on the examined region of the patient;

individually designating a specific one of the patients;

reading out the past scan condition of the designated specific one of the patients from the scan condition file means;

setting a scan condition in accordance with the past scan condition of the examined region of the designated patient; and performing the scanning operation on the examined region of the designated patient in accordance with the set scan condition.

7. A method of performing a scanning operation according to claim 6, wherein said at least one scanning operation on the examined region of the patient is previously performed by the steps of:

preparing an information of the patient;

entering the information into the main controller;

carrying out a scanographing operation and displaying the scanographic image on the monitor;

indexing the past scan condition of the patient from the scan condition file;

confirming whether the past scan condition is indexed;

converting a slice information in the indexed past scan condition into a slice information image data in a case where the past scan condition is indexed;

displaying the indexed past scan condition as numerical data and displaying the slice information as slice information image data;

confirming whether a scanning condition is set in accordance with the displayed past scan condition;

inversely converting the slice information image data into the slice information;

setting and storing the scanning condition in a case where the scanning condition is set in accordance with the displayed past scan condition; and performing the scanning operation with the set scanning condition.

8. A method of performing a scanning operation according to claim 7, wherein said scanning operation further comprises the step of modifying a numerical data of the scanning condition in the displayed past scan condition.

9. A method of performing a scanning operation according to claim 7, wherein in a case where the past scan condition is not indexed, the scanning condition is set manually and stored and the scanning operation is then performed with the set scanning condition.

10. A method of performing a scanning operation according to claim 7, wherein in a case where the scanning condition is not set, it is confirmed whether further index is to be continued, and in a case where the index is continued, another past scan condition for the patient is further indexed, and in a case where the index is not continued, the scanning condition is set manually and stored.

11. A method of performing a scanning operation according to claim 7, wherein the slice information includes slicing pitch and a tilt angle of a gantry of the X-ray CT apparatus.

12. A method of performing a scanning operation according to claim 7, wherein a predetermined number of a plurality of past scan condition for the patient are stored in accordance with the time order and when a new scanning condition is stored as past scan condition, an oldest past scan condition automatically vanishes.

13. A method of performing a scanning operation according to claim 6, wherein said scanning operation is performed by the steps of:

preparing an information of the patient;

entering the information into the main controller;

indexing the past scan condition of the patient from the scan condition file;

confirming whether the past scan condition is indexed;

displaying the indexed past scan condition as numerical data in a case where the past scan condition is indexed;

confirming whether a scanning condition is set in accordance with the displayed past scan condition;

setting and storing the scanning condition in a case where the scanning condition is set in accordance with the display past scan condition; and performing the scanning operation with the set scanning condition.

14. A method of performing a scanning operation according to claim 13, wherein said scanning operation further comprises the step of modifying a numerical data of the scanning condition in the displayed past scan condition.

15. A method of performing a scanning operation according to claim 13, wherein in a case where the past scan condition is not indexed, the scanning condition is set manually and stored and the scanning operation is then performed with the set scanning condition.

16. A method of performing a scanning operation according to claim 13, wherein in a case where the scanning condition is not set, it is confirmed whether further index is to be continued, and in a case where the index is continued, another past scan condition for the patient is further indexed, and in a case where the index is not continued, the scanning condition is set manually and stored.

17. A method of performing a scanning operation according to claim 13, wherein a predetermined number of a plurality of past scan condition for the patient are stored in accordance with the time order and when a new scanning condition is stored as past scan condition, an oldest past scan condition automatically vanishes.

18. A method of performing a scanning operation according to claim 6, wherein each of said past scan condition includes a number of scans, a scanned area, a tube voltage of the X-ray tube, and a tube current of the X-ray tube.

* * * * *